(12) United States Patent
Glazer

(10) Patent No.: US 7,090,395 B2
(45) Date of Patent: Aug. 15, 2006

(54) WIRELESS DIGITAL DENTAL X-RAY SENSOR WITH POSITIONING APPARATUS

(76) Inventor: Dov Glazer, 3525 Prytania St., Suite 312, New Orleans, LA (US) 70115

( * ) Notice: Subject to any disclaimer, the term of this patent is extended or adjusted under 35 U.S.C. 154(b) by 0 days.

(21) Appl. No.: 11/099,411

(22) Filed: Apr. 5, 2005

(65) Prior Publication Data

US 2005/0220272 A1  Oct. 6, 2005

Related U.S. Application Data

(60) Provisional application No. 60/559,578, filed on Apr. 5, 2004.

(51) Int. Cl.
*A61B 6/14* (2006.01)
(52) U.S. Cl. ........................ 378/191; 433/29
(58) Field of Classification Search ................. 378/62, 378/63, 168, 170, 189, 191, 169, 38–40; 433/29; 250/370.09
See application file for complete search history.

(56) References Cited

U.S. PATENT DOCUMENTS

| RE25,773 | E | * | 5/1965 | Medwedeff et al. ........ 378/170 |
| 4,160,997 | A | | 7/1979 | Schwartz |
| 5,119,410 | A | * | 6/1992 | Donato ........................ 378/170 |
| 5,434,418 | A | | 7/1995 | Schick |
| 5,500,884 | A | * | 3/1996 | Guenther et al. ............. 378/38 |
| 5,799,058 | A | * | 8/1998 | Willis et al. ................ 378/168 |
| 5,844,961 | A | * | 12/1998 | McEvoy et al. ........... 378/98.8 |
| 2003/0156681 | A1 | | 8/2003 | Cianiosi et al. |
| 2004/0005032 | A1 | | 1/2004 | Eros |

* cited by examiner

*Primary Examiner*—Edward J. Glick
*Assistant Examiner*—Anastasia S. Midkiff
(74) *Attorney, Agent, or Firm*—Blynn L. Shideler; Krisanne Shideler; BLK Law Group

(57) ABSTRACT

A universal integrated wireless digital dental x-ray sensor and positioning apparatus includes a digital array sensor, such as CCD or CMOS, attached to a distal end of a bite block portion through a hinge assembly. Attached to an opposite end of the bite block portion is a housing. The housing houses the electrical components which includes the digital imaging processing unit, a wireless transmitting unit, a power source for operating the electronics and a coupling for recharging the power source. An on-board viewer may be in the housing. The electrical components are coupled to the sensor through wires embedded within the bite block portion and extending through the hinge assembly. A target x-ray member is attached to the tubular housing for proper direction of the x-rays onto the sensor.

20 Claims, 3 Drawing Sheets

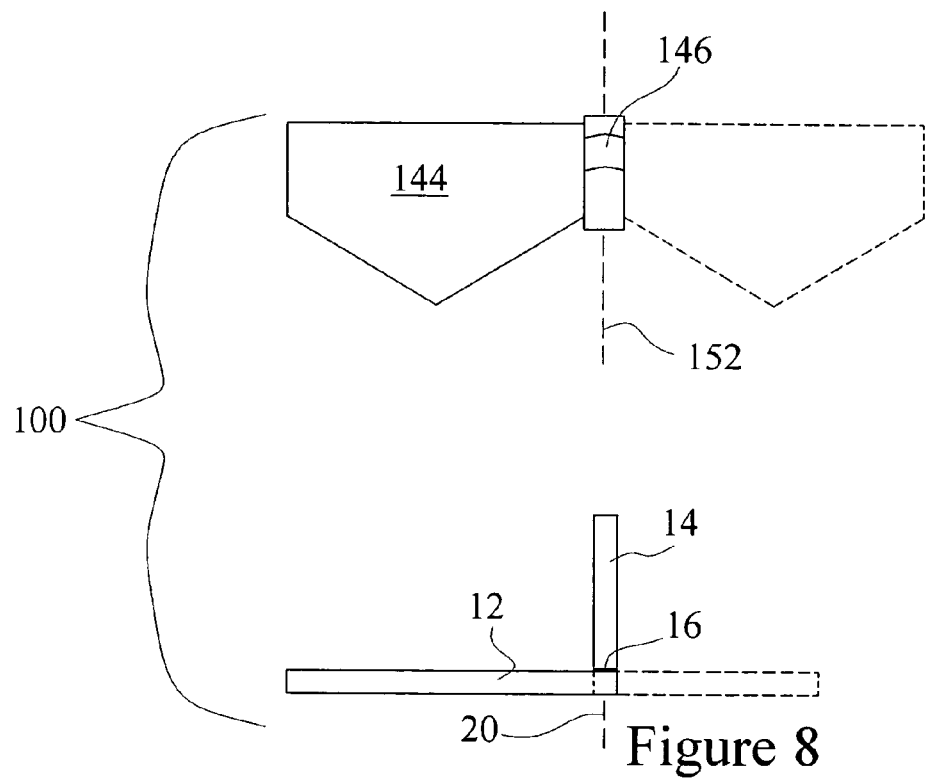
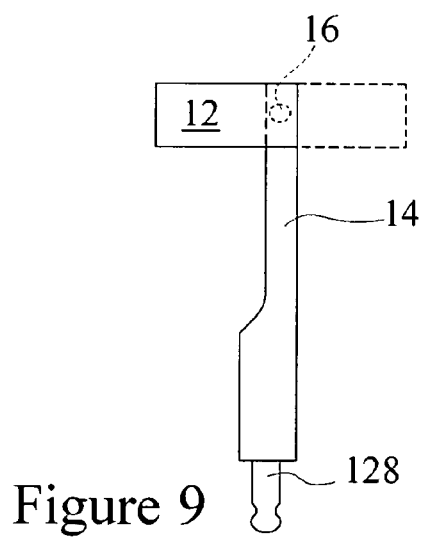
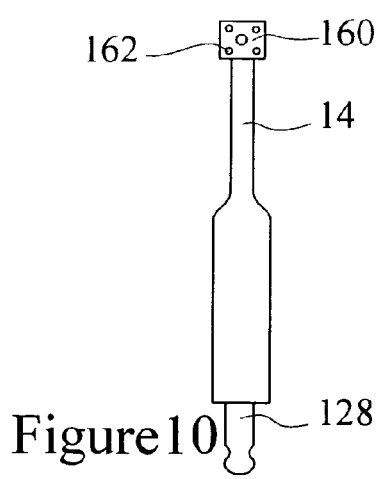

WIRELESS DIGITAL DENTAL X-RAY SENSOR WITH POSITIONING APPARATUS

This application claims the benefit of provisional patent application Ser. No. 60/559,578, entitled "Wireless Digital Dental X-Ray Sensor with Positioning Apparatus" filed Apr. 5, 2004.

BACKGROUND OF THE INVENTION

1. Field of the Invention

The invention relates to digital dental x-ray devices. Specifically, the invention relates to an integrated wireless digital dental x-ray sensor, optional on-board viewer and positioning apparatus.

2. Background Information

Dentists and oral surgeons have historically used light and x-radiation ("x-rays") to obtain and then store images of their patients' teeth, mouths and gums to aid in diagnosis of a patient. In traditional oral and dental radiography, a cartridge containing a piece of radiographic film is placed in the patient's mouth, for example behind a patient's tooth, and an x-ray beam is projected through the tooth and onto the film. The film, after being exposed in this manner, is developed in a dark room or a closed processor using special chemicals to obtain a radiographic image of the tooth.

More recently, the field of film-less dental radiography has emerged. In film-less dental radiography, an x-ray beam is projected through the patient's teeth in the same manner as in the film based methods, but no x-ray sensitive film is used. Instead, an electronic sensor is placed in the patient's mouth behind the tooth to be examined. The electronic sensor may include a charge-coupled device (CCD), a complementary metal oxide semi conductor (CMOS), or any other film-less radiation sensor. The x-rays pass through the teeth and impinge on the electronic sensor, which converts the x-rays into an electrical signal. The electrical signal is often transmitted over a wire to a computer, either directly or though a module containing intermediate processing circuitry. The computer then processes the signal to produce an image on an associated output device, such as a monitor or a printer.

Film-less dental radiography offers several advantages over traditional film-based radiography. First, the electronic sensor is much more sensitive to x-rays than is film, allowing the dosage of x-rays to the patient to be lowered. Also, the image of the tooth is generated by the computer almost instantaneously, thus eliminating the entire film developing process. The operator can quickly determine in real time if the image is the one required for proper diagnosis of the patient or if further imaging is required. In addition, because the images are generated electronically, they can be stored electronically in a computer database. Examples of film-less dental radiography systems include those described in U.S. Pat. No. 4,160,997 to Robert Schwartz, U.S. Pat. No. 5,434,418 to David Schick, and U.S. Published Patent Application No. 2003/0156681 to Egidio Cianciosi et al. These systems can be generally referred to as digital dental x-ray devices. U.S. Published Patent Application No. 2004/0005032 to Nanni Eros discloses a digital dental device in which the sensor communicates with the computer through a wireless connection.

When taking intra-oral film radiographs, a conventional standard of care is to use a paralleling device, a popular version of which is known as the Rinn Instrument (see at www.rinncorp.com). In taking x-rays of all of a patient's teeth, also known as a "Complete Mouth Series", typically three different x-ray film holders are employed. In addition, the holder for taking periapical films of the upper right and lower left teeth is disassembled and then reassembled in a different configuration to take films of the upper left and lower right teeth. Further, in order to take an x-ray of a tooth undergoing root canal treatment, an additional x-ray holder is used. Furthermore, in some situations the paralleling technique is not possible or practical. Consequently, up to seven different holders are currently used to take dental x-rays.

The existing digital dental devices do not have adequate universal structure for proper positioning of the sensor within the patient's mouth, nor do they provide convenient location or housing of the digital imaging components. Further, there is no existing digital dental device that provides viewing integrated with the sensor. It is an object of the present invention to overcome the deficiencies of these prior art digital dental x-ray devices, and to overcome the deficiencies of these prior art film and digital sensor holders, in order to provide an integrated wireless digital dental x-ray sensor and positioning apparatus providing an efficient, effective device. A further object of the present invention is to provide a single universal positioning device with which any of a patients teeth can be radio-graphed as desired by the operator.

SUMMARY OF THE INVENTION

At least some of the above problems with the prior art related to conventional film x-radiography, wired digital x-radiography, and the holders and positioning apparatus used in capturing and storing x-radiographic images, are addressed with an integrated wireless digital dental x-ray sensor and positioning apparatus according to the present invention. The apparatus according to the present invention includes a digital array sensor, such as CCD or CMOS, attached to a distal end of a bite block portion through a hinge assembly. The hinge assembly may be a double hinge allowing rotation of the sensor about two orthogonal pivot axes. Attached to an opposite end of the bite block portion is a housing, such as a tubular housing. The tubular housing houses the electrical components, which includes the digital imaging processing unit, a wireless transmitting unit, a power source for operating the electronics, and a coupling for recharging the power source. The electrical components are coupled to the sensor through wires embedded within the bite block portion and extending through the hinge assembly. A target x-ray ring is attached to the side of the tubular housing for proper direction of the x-rays onto the sensor.

The present invention may further include an eccentric offset pivoting connection for the target ring to allow for aligning the target in proper position based upon the position of the sensor. The present invention may include an articulation joint in the bite block portion for angular positioning thereof to provide further versatility to the apparatus of the present invention.

The present invention may include an "on-board" viewer in the housing and coupled to the sensor. The term "on-board" within the meaning of this specification means that the viewer is integrated into the sensor and bite block elements. The present invention may include a removable target alignment mechanism attached to the housing that aligns with the sensor to allow the user to properly align the X-ray machine relative to the sensor. The present invention may provide that the sensor and target are removable from the housing, wherein the housing may receive other components, such as an intra-oral camera.

These and other advantages of the present invention will be clarified in the description of the preferred embodiment taken together with the attached figures wherein like reference numerals represent like elements throughout.

BRIEF DESCRIPTION OF THE DRAWINGS

FIG. 8 is a schematic front view of the digital array sensor and target of the apparatus of FIG. 7;

FIG. 9 is a schematic side view of the digital array sensor and bite block portion of the apparatus of FIG. 7; and FIG. 10 is a schematic side view of an intra-oral camera portion for use with the apparatus of FIG. 7.

DETAILED DESCRIPTION OF THE PREFERRED EMBODIMENT

Figure 1:
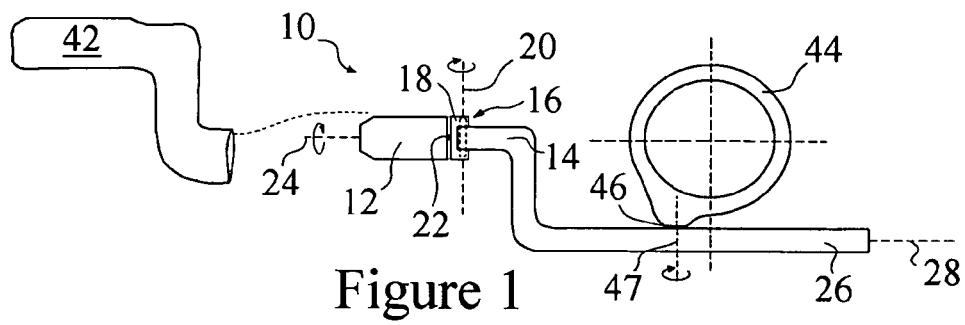
FIG. 1 is a schematic plan view of an integrated wireless digital dental x-ray sensor and positioning apparatus according to a first embodiment of the present invention with the elements in a stored, in-operative position.
Figure 2:
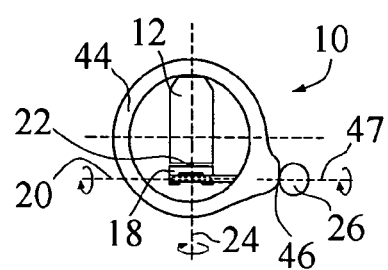
FIG. 2 is a schematic rear view of the integrated wireless digital dental x-ray sensor and positioning apparatus of FIG. 1 in a first operative position.
Figure 4:
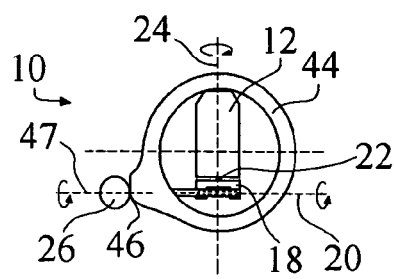
FIG. 4 is a schematic rear view of the integrated wireless digital dental x-ray sensor and positioning apparatus of FIG. 1 in a second operative position.
Figure 3:
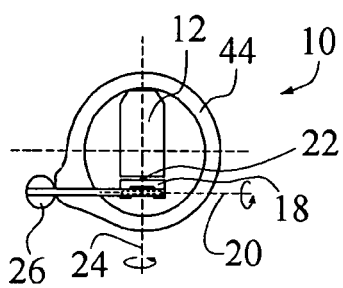
FIG. 3 is a schematic front view of the integrated wireless digital dental x-ray sensor and positioning apparatus of FIG. 2.
Figure 5:
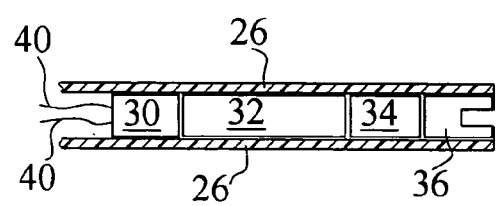
FIG. 5 is an enlarged sectional schematic view of a tubular housing of the integrated wireless digital dental x-ray sensor and positioning apparatus of FIG. 1.

FIGS. 1–5 schematically illustrate an integrated wireless digital dental x-ray sensor and positioning apparatus or assembly 10 according to one aspect of the present invention with the elements in a stored, in-operative position. Essentially all of the elements in FIG. 1 are aligned in one plane, which is useful for storage and shipment of the apparatus 10 and for illustrating the elements thereof. FIGS. 2 and 3 schematically illustrate a first operative position and FIG. 4 schematically illustrates a second operative position of the integrated wireless digital dental x-ray sensor and positioning apparatus 10 of FIG. 1. The apparatus 10 according to the present invention includes a digital array sensor 12 attached to a distal end of a bite block portion 14 through a hinge assembly 16. The sensor 12 is preferably of CCD or CMOS type, but other x-ray sensitive digital arrays, also called film-less radio sensors, could be utilized.

The bite block portion 14 is a generally flat or planar member formed of plastic or any suitable material. The bite block portion 14 is of minimum thickness that is sized to properly position the sensor 12 within the patient's mouth. There is flexibility to the specific shape of the bite block portion 14 in plan view. In other words the plan outline of the bite block portion 14 may take numerous shapes without effecting the operation of the present invention. The hinge assembly 16 is a double hinge allowing rotation of the sensor 12 about two orthogonal pivot axes. Specifically a first hinge pin 18 is attached to the bite block portion 14 and defines a first pivot axis 20 for the sensor 12. The sensor 12 is coupled to the pin 18 through a rotational coupling or pin 22 that defines a second pivot axis 24. As shown in the figures the pivot axis 20 and 24 are orthogonal to each other with the pivot axis 24 generally parallel to or aligned with the longitudinal axis of the sensor 12. The hinge assembly 16 is substantially similar to that found in contemporary digital camera phones having a pivoting flip top view screen.

Attached to an opposite end of the bite block portion 14 from the hinge assembly 16 is an integral tubular housing 26 extending along a longitudinal axis 28 of the assembly 10. The tubular housing 26 may be formed of plastic, or any conventional material, and houses the electrical components of the assembly 10. The electrical components of the assembly 10 are shown schematically in FIG. 5 and include a digital imaging processing unit 30, a wireless transmitting unit 32, a power source 34 for operating the electronics and a coupling 36 for recharging the power source. The digital imaging processing unit 30 is a conventional electronic component the specifics of which will depend upon the specific sensor 12 being utilized. The wireless transmitting unit 32 is a conventional wireless transmitter such as using Bluetooth wireless technology or Wi-Fi standard technology or other appropriate wireless technology. Wi-Fi is a contraction of wireless fidelity and represents a dominant standard in wireless transmissions. Bluetooth technology is compatible with Wi-Fi and often used for applications having smaller range applications. Other wireless technologies could also be employed as will be understood by those of ordinary skill in the art. The power source 34 is a rechargeable battery pack with the coupling 36 being adapted to be received in a recharging docking station 38 (shown in FIG. 6). It is contemplated that the coupling 36 could be eliminated and replaceable batteries used in the assembly 10. A further modification of this aspect of the present invention is the attachment of the assembly to a remote viewing device or receiver 52 (as opposed to an on-board viewer shown in FIG. 7 discussed below), such as a lap top or desk top computer with appropriate wiring 58 as shown in phantom in FIG. 6 as an alternative. The wiring 58 can be used as both a power source for the assembly 10 and for the transmission of data to the receiver 52. This alternative embodiment would effectively eliminate the coupling 36, power source 34 and wireless transmitting unit 32 from the housing 26 providing a simpler, but more restrictive design. In this alternative the data input of the wiring 58 can take the form of any number of standard conventional input configurations (e.g. USB port). The power source may be through the receiver in this alternative embodiment or may extend to a separate source (e.g. a conventional wall plug). The details of hard wiring a device such as the apparatus 10 are believed to be well known to those of ordinary skill in the art.

The digital imaging processing unit 30 is coupled to the sensor 12 through wires 40 embedded within the bite block portion 14 and extending through the hinge assembly 16. A replaceable, disposable, protective, radio transparent, flexible sheath 42 can be added over the end of the assembly 10 received in the patient's mouth to make the assembly easily reusable. With the sheath 42, the sheath can be disposed from patient to patient with the assembly 10 quickly and easily reused between patients.

A target x-ray member, such as ring 44, is attached to the side of the housing 26 for proper direction of the x-rays onto the sensor 12. The ring 44 is attached to the housing 26 through a pivot or hinge connection 46 with the ring 44 offset or eccentric to the axis 47 of the hinge 46. The offset of the ring 44 allows the ring 44 to be shifted in position relative to the axis 28 of the assembly 10.

An additional advantage of the apparatus 10 over conventional digital x-ray systems is through the inclusion of optional "positional sensors", or mini-switches, located at each articulating element (e.g. 18, 22, 46 and 48 (discussed below)). Information is sent from each articulating element to the processing unit 30, to indicate the relative position each articulated segment. With current software systems, a predetermined template is chosen prior to taking the digital x-rays, so that when the x-rays are "exposed" they are positioned in the proper location for viewing. For example, x-rays taken in the upper right quadrant of the mouth are positioned in the upper right section of the template and x-rays of the anterior teeth are positioned in the center of the template. If an x-ray is not taken in proper sequence in the prior art systems, it will be positioned in the wrong place on the template. With the inclusion of positional sensors in the apparatus 10, the software of the apparatus 10 can "read" the position of the components of the apparatus and thus automatically determine the correct location to place the exposed image.

Figure 6:
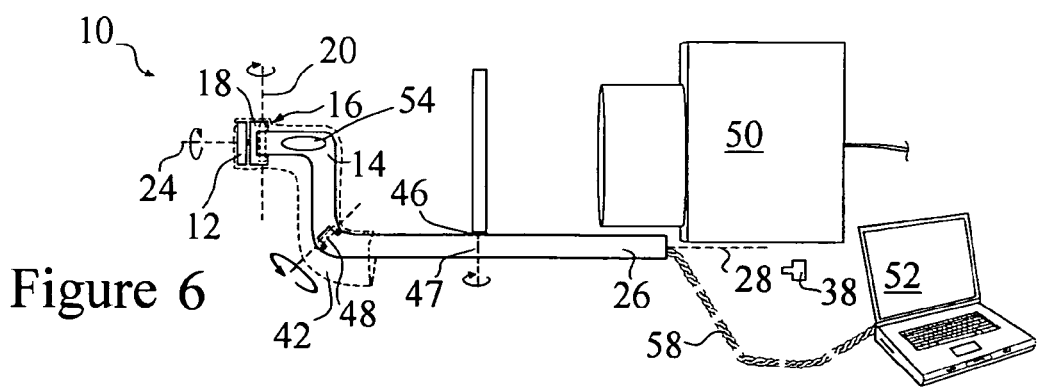
FIG. 6 is a schematic plan view of an integrated wireless digital dental x-ray sensor and positioning apparatus according to a second embodiment of the present invention with the elements in an aligned operative position and illustrating the remaining radiographic elements used with the apparatus.

FIG. 6 illustrates a modified assembly 10, in an operative position (in that the target ring 44 is aligned with the sensor array 12), in which the bite block portion 14 includes an articulating joint 48, which allows for further positioning of the sensor 12 within the patient. This positioning, intended for capturing images of the upper and lower teeth simultaneously, is commonly referred to as the "bite-wing" position, while FIGS. 2, 3, and 4 illustrate the positioning for "periapical radiographs". FIG. 6 also shows the conventional x-ray components used with the assembly 10. Other shapes for the bite block portion 14 and further articulation could be provided to add greater flexibility to the integrated device. The simplicity of the assembly 10 in FIG. 1 is more advantageous from a cost perspective than the additional articulation provided in the assembly of FIG. 6.

A further aspect of the present invention is the provision of an adequately sized hole 54 in the center of bite block portion 14. This space, or hole 54, permits the seating of the apparatus 10 while root canal files are retained in a patients tooth during endodontic treatment.

In operation, the assembly is removed from the docking station 38 and a new sterilized sheath 42 is placed over the end of the assembly 10. The sensor 12 is rotated about axis 24 and 20 to a desired position. The pin 18 allows the sensor 12 to rotate about 180 degrees to opposite sides of the bite block portion 14 rotating about axis 20 while the pin 22 allows angular rotation of the sensor 12 about the axis 24. With the sensor 12 in a desired location the x-ray ring 44 is positioned to align therewith. The sensor 12 is then placed in the patient's mouth and the x-rays transmitted at the sensor 12 through the target ring 44 using conventional x-ray devices 50 shown in FIG. 6. The digital image formed by the sensor 12 is processed by the processing unit 30 and transmitted through wireless transmitter 32 to receiver 52. The receiver 52 may be a desktop computer, a laptop or a printing device or any device that has an associated wireless receiver therewith. It should be noted that Wi-Fi and Bluetooth technology wireless transmitter receivers are being incorporated into laptops, PDA's and other electrical devices. An important advantage that the universal digital dental radiographic assembly 10 has over conventional methods for accurately exposing radiographic film is that with one single assembly 10 all the teeth of a patient can be radio-graphed. The apparatus 10 eliminates the need for the time consuming processes of changing holders as in the prior art. With this universal apparatus 10, by simply rotating sensor 12 and changing the angulations of the aiming ring 44, all possible positions are quickly achieved. The use of positional sensors for the hinges allows the apparatus 10 to automatically, properly sort or identify each image.

Figure 7:
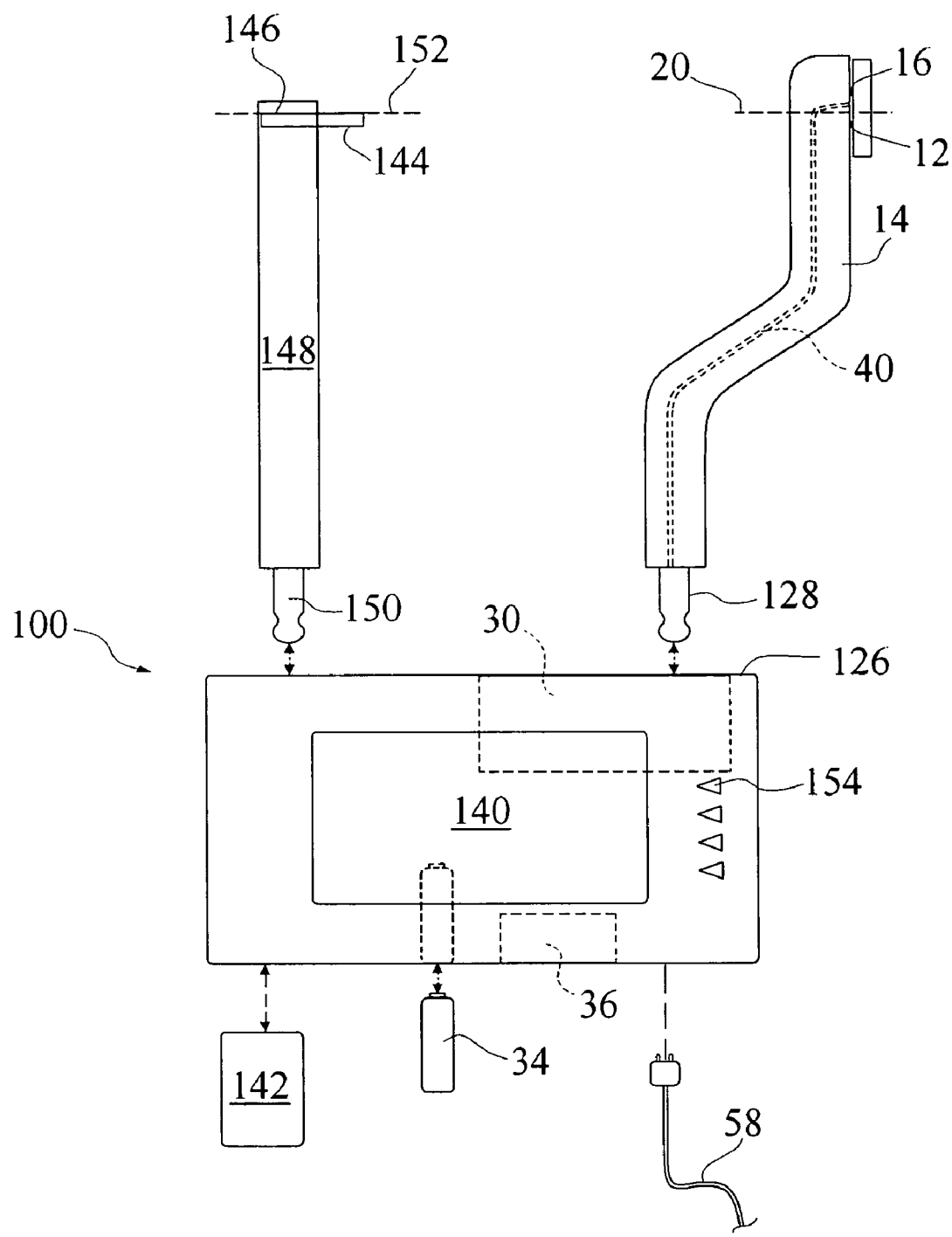
FIG. 7 is a schematic exploded view of an integrated wireless digital dental x-ray sensor and positioning apparatus according to a third embodiment of the present invention with the elements in an aligned operative position.

FIGS. 7–9 schematically illustrate an integrated digital dental x-ray sensor and positioning apparatus or assembly 100 according to a third embodiment of the present invention. The apparatus 100 is similar to apparatus 10 described above. The apparatus 100 according to the present invention includes a digital array sensor 12 attached to a distal end of a bite block portion 14 through a hinge assembly 16.

As described above, the sensor 12 is preferably of CCD or CMOS type, but other x-ray sensitive digital arrays, also called film-less radio sensors, could be utilized. The bite block portion 14 is a generally flat or planar member formed of plastic or any suitable material. The bite block portion 14 is of minimum thickness that is sized to properly position the sensor 12 within the patient's mouth. The hinge assembly 16 defines a pivot axis 20 for the sensor 12.

The bite block portion 14 and sensor 12 are removably attached to a housing 126, such as by plug 128. The housing 126 may be formed of plastic, or any conventional material, and houses the electrical components of the assembly 100. When the bite block portion 14 and sensor 12 is attached to, i.e. plugged into, the housing 126, these elements are considered integral thereto. The electrical components of the assembly 100, such as shown schematically in FIG. 5, may include a digital imaging processing unit 30, a wireless transmitting unit 32, a power source 34 (e.g. replaceable/rechargeable batteries) for operating the electronics and a coupling 36 for recharging the power source. Further, the electrical components in the housing 126 include an "on board" viewer 140 for viewing the associated image directly on the assembly 100.

The digital imaging processing unit 30 of the apparatus 100 is coupled to the sensor 12 through wires 40 embedded within the bite block portion 14 and extending through the hinge assembly 16 as described above in connection with assembly 10. Alternately, the digital imaging processing unit 30 of the apparatus 100 is coupled to the sensor 12 through wires 40 embedded within housing 126 as described above in connection with assembly 10. The replaceable, disposable, protective, radio transparent, flexible sheath 42 can be added over the sensor 12 end of the assembly 100 which is received in the patient's mouth to make the assembly easily reusable. With the sheath 42, the sheath 42 can be disposed from patient to patient with the assembly 100 quickly and easily reused between patients.

A target x-ray member, such as platform 144, is attached to the housing 126 for proper direction of the x-rays onto the sensor 12. The platform 144 is attached to a post 148 through a pivot or hinge connection 146 with the platform 144. The post 148 has a plug 150 similar to the plug 128 for attaching the post 148 to the housing 126 (except the plug 148 need not have any electrical connections). The hinge 146 allows the platform 144 to be shifted in position relative to the axis 152 to align with sensor 12 as shown in FIG. 8. This alignment allows the x-ray device 50 to be easily positioned in use as discussed above. This embodiment illustrates that the target, platform 144, need not be a ring shape to be operative.

With the on-board viewer 140 the assembly could operate as a stand alone device. The doctor can view the images directly on the viewer 140. The images can be stored and transferred from the housing 126 with a memory card 142, similar to those found in commercial digital cameras. Controls 154 allow the operator to operate the assembly as desired, e.g. cycle through images, power on and off, enlarge a given image, etc. Essentially the housing 126 can be considered the functional equivalent of a digital camera wherein the digital input for the images comes from the sensor 12.

The apparatus 100 also allows for the inclusion of optional "positional sensors", or mini-switches, located at each articulating element (e.g. hinges 116 and 146). Information is sent from each articulating element to the processing unit 30, to indicate the relative position each articulated segment.

The apparatus 100 can be easily used for other purposes, such as a viewer for an intra-oral digital camera. FIG. 10 illustrates a digital camera lens 160, with associated lights 162 (such as white LED or infrared LED members) that is attached to a apparatus 100 with a plug 128 for coupling to the housing 126 (when the sensor 12 and associated bite block 14 has been removed). The apparatus 100 can serve as a base supporting intra oral videography and digital x-rays. As with assembly 10 discussed above, replaceable batteries may be used in the assembly 100. Further, a remote viewing device or receiver 52, shown in FIG. 6 (as opposed to the on-board viewer 140 shown in FIG. 7), such as a lap top or desk top computer, may be used with apparatus 100 through appropriate wiring 58. The wiring 58 can be used as both a power source for the assembly 100 and for the transmission of data to the receiver 52.

The invention has been described with reference to the preferred embodiment. Obvious modifications and alterations will occur to others upon reading and understanding the proceeding detailed description. It is intended that the invention be construed as including all such modifications and alterations. The scope of the present invention is intended to be construed in connection with the attached claims and equivalents thereto.

What is claimed is:

1. A digital dental x-ray sensor and positioning apparatus comprising:
   a bite block portion;
   a hinge assembly at a distal end of the bite block portion;
   a digital array sensor attached to a distal end of a bite block portion through the hinge assembly, wherein the digital array sensor is pivoted to a variety of operative positions relative to the bite block portion;
   a housing attached to an opposite end of the bite block portion;
   electrical components which are associated with the digital array sensor housed within the housing, the electrical components including a digital imaging processing unit; and
   a target x-ray member moveably mounted to the housing and adapted to be aligned with the digital array sensor for proper direction of x-rays onto the digital array sensor.

2. The digital dental x-ray sensor and positioning apparatus of claim 1 further including an eccentric offset pivoting connection between the target x-ray member and the housing to allow for aligning the target x-ray member in proper position based upon the position of the digital array sensor.

3. The digital dental x-ray sensor and positioning apparatus of claim 1 further including an articulation joint in the bite block portion for angular positioning thereof.

4. The digital dental x-ray sensor and positioning apparatus of claim 1 wherein the hinge assembly is a double hinge allowing rotation of the digital away sensor about two orthogonal pivot axes.

5. The digital dental x-ray sensor and positioning apparatus of claim 1 wherein at least the hinge assembly contains positional sensors to automatically indicate the operative position of the digital array sensor relative to the bite block portion.

6. A wireless digital dental x-ray sensor and positioning apparatus comprising:
   a bite block portion;
   a hinge assembly at a distal end of the bite block portion;
   a digital array sensor attached to a distal end of a bite block portion through the hinge assembly, wherein the digital array sensor is pivoted to a variety of operative positions relative to the bite block portion;
   a housing attachable to an opposite end of the bite block portion; and
   electrical components which are associated with the digital array sensor housed within the housing, the electrical components including a digital imaging processing unit and a wireless transmitting unit.

7. The wireless digital dental x-ray sensor and positioning apparatus of claim 6 further including a target x-ray member moveably mounted to the housing and adapted to be aligned with the digital away sensor for proper direction of x-rays onto the digital array sensor.

8. The wireless digital dental x-ray sensor and positioning apparatus of claim 6 wherein the electrical components are coupled to the digital array sensor through wires embedded within the bite block portion and extending through the hinge assembly.

9. The wireless digital dental x-ray sensor and positioning apparatus of claim 6 wherein the hinge assembly is a double hinge allowing rotation of the digital array sensor about two orthogonal pivot axes.

10. The wireless digital dental x-ray sensor and positioning apparatus of claim 6 further including a disposable, flexible sheath covering the digital array sensor and bite block portion in use.

11. The wireless digital dental x-ray sensor and positioning apparatus of claim 6 wherein at least the hinge assembly contains positional sensors to automatically indicate the operative position of the digital array sensor relative to the bite block portion.

12. A digital dental x-ray sensor and positioning apparatus comprising:
    a bite block portion;
    a digital array sensor attached to a distal end of a bite block portion;
    a housing attached to an opposite end of the bite block portion;
    electrical components which are associated with the digital array sensor housed within the housing, the electrical components including a digital imaging processing unit; and
    a target x-ray member mounted on the housing and adapted to be aligned with the digital array sensor for proper direction of x-rays onto the digital array sensor.

13. The digital dental x-ray sensor and positioning apparatus of claim 12 wherein the electrical components further include a wireless transmitting unit.

14. The digital dental x-ray sensor and positioning apparatus of claim 12 further including an integral on-board viewer in the housing for at least viewing images from the array.

15. The digital dental x-ray sensor and positioning apparatus of claim 14 further including a digital camera lens configured for attachment to the housing for providing intra-oral video images.

16. The digital dental x-ray sensor and positioning apparatus of claim 12 wherein the digital array sensor is one of a CCD or a CMOS type sensor, and the sensor and bite block portion is removably attached to the housing.

17. The digital dental x-ray sensor and positioning apparatus of claim 12 further including a sheath covering the digital array sensor and bite block portion.

18. The digital dental x-ray sensor and positioning apparatus of claim 12 further including external wiring extending from the electrical components to an external viewing device.

19. The digital dental x-ray sensor and positioning apparatus of claim 12 further including a hole in the bite block portion to accommodate use of the apparatus in root canal operations.

20. The digital dental x-ray sensor and positioning apparatus of claim 12 wherein the bite block portion is generally planar.

* * * * *